United States Patent [19]

Biere

[11] Patent Number: 4,705,856
[45] Date of Patent: Nov. 10, 1987

[54] PROCESS FOR PRODUCING β-CARBOLINE DERIVATIVES

[75] Inventor: Helmut Biere, Berlin, Fed. Rep. of Germany

[73] Assignee: Schering Aktiengesellschaft, Berlin and Bergkamen, Fed. Rep. of Germany

[21] Appl. No.: 546,356

[22] Filed: Oct. 28, 1983

[30] Foreign Application Priority Data

Oct. 29, 1982 [DE] Fed. Rep. of Germany ....... 3240511

[51] Int. Cl.⁴ ................. C07F 9/65; C07D 471/04; C07D 401/14
[52] U.S. Cl. ........................ 546/21; 546/85; 546/86; 546/87; 546/65; 544/361; 544/126
[58] Field of Search .............. 546/21, 86, 87, 85, 546/65; 544/361, 126

[56] References Cited

FOREIGN PATENT DOCUMENTS 42-24917 11/1967 Japan ........................... 546/85

*Primary Examiner*—Henry R. Jiles
*Assistant Examiner*—J. Richter
*Attorney, Agent, or Firm*—Millen & White

[57] ABSTRACT

β-carbolines of formula I

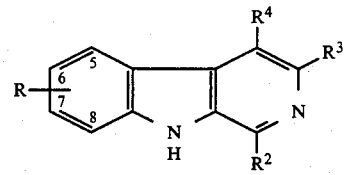

can be prepared by reacting an indole of formula II:

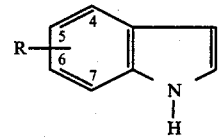

with an azabutadiene of formula III

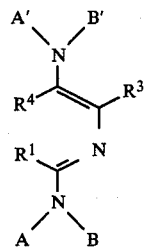

in the presence of an acid at 50°–200° C.

15 Claims, No Drawings

PROCESS FOR PRODUCING β-CARBOLINE DERIVATIVES

CROSS REFERENCE TO RELATED APPLICATION

This application is related to commonly assigned U.S. Ser. No. 547,555, filed on even date, and whose entire disclosure is incorporated by reference herein.

BACKGROUND OF THE INVENTION

This invention relates to a process for producing β-carboline derivatives.

Carboline derivatives, especially substituted β-carboline derivatives, have recently aroused great interest in pharmacological research since they exert a wealth of therapeutically useful effects on the central nervous system. For example, they display anticonvulsive, anxiolytic, muscle relaxing and/or sedative effects.

The importance that is given to this class of substances is further reflected in the great number of patent applications filed, of which the following are examples: DE-OS No. 30 15 816, DE-OS No. 30 23 567, DE-OS No. 30 48 318 and U.S. Pat. No. 3,202,667.

The processes that are described in the literature for production of β-carbolines have the drawback that they go through several stages and are not always satisfactory in yield (R. A. Abramovitch and J. D. Spenser, Advances in Heterocycl. Chemistry, Vol. 3, p. 79).

A typical carboline synthesis can be summarized by the following diagram.

Scheme of formulas

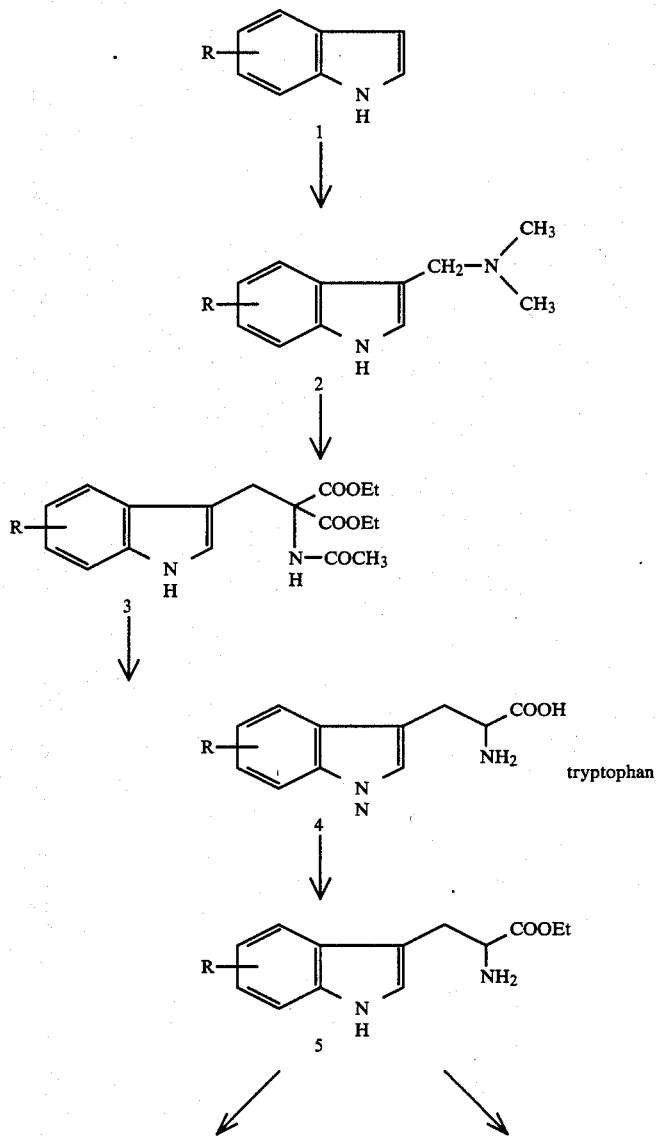

-continued
Scheme of formulas

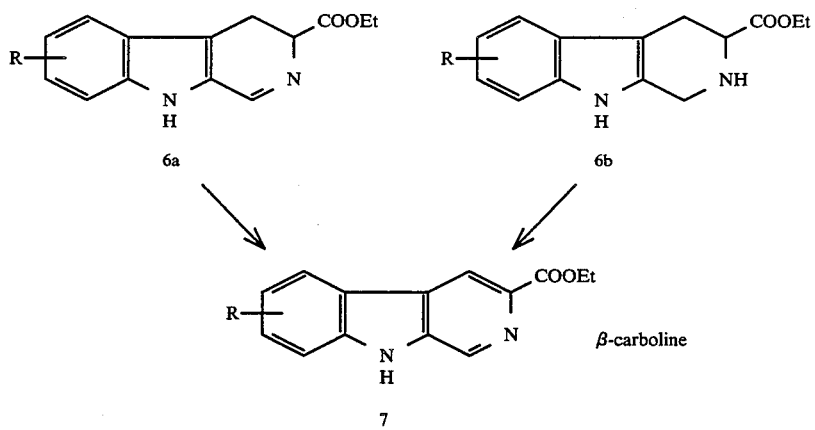

Starting with indole (1), gramine or a compound analogous to gramine (2) is produced by reaction with formaldehyde and a secondary amine. This is converted into a tryptophan precursor (3) by reaction with acetoamidomalonic ester under basic catalysis.

Racemic tryptophan (4) is formed after elimination of all protective groups and decarboxylation. Tryptophan ester (5) is formed after esterification, from which a 3,4-dihydro-β-carboline (6a) is formed after acylation of the amino group and cyclization under Bischler-Napieralski reaction conditions. A tetrahydro-β-carboline (6b) is formed according to Pictet-Spengler. It is converted into the carbolines (7) after dehydration.

Apart from the large number of synthesis steps with the inevitable loss of time and yield, the cyclizations according to Bischler-Napieralski and Pictet-Spengler, cause special problems. Despite numerous improvements in these processes, only a slight yield results, whereby sensitive, partially hydrogenated intermediate products are formed which can cause various secondary reactions. Also, the dehydrogenation reaction to form di- and tetrahydrocarbolines often results in a low yield.

For this reason, it would be considered a particularly important advance in process engineering, if it were possible to perform a ring closure reaction on unsaturated indole precursors, exemplified by dehydrotryptophan derivatives, whereby a simple production process would be a prerequisite for the required dehydrotryptophan derivatives.

It would be a further important advance in process engineering, if it were possible to perform this ring closure reaction on a dehydrotryptophan derivative in such a way that the aromatic carboline system would be formed instead of a 1,2-dihydrocarboline derivative.

An optimal variant process for formation of carbolines would also require that it combine the above mentioned requirements and aims in the performance of a reaction which still takes place regiospecifically; this means that the hypothetical reaction, for example, would provide the desired β-carboline exclusively, without contamination with other carbolines.

SUMMARY OF THE INVENTION

It is an object of this invention to provide a process which fulfills the requirements of the advances mentioned above.

Upon further study of the specification and appended claims, further objects and advantages of this invention will become apparent to those skilled in the art.

These objects have been attained by providing a process for producing β-carboline derivatives of formula I:

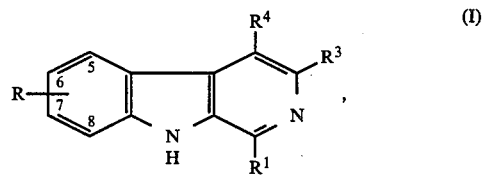

wherein
R is hydrogen, one or two of halogen atoms or any organic radicals in 5-, 6-, 7- or 8-position(s), $R^1$ and $R^4$ are the same or different and each is hydrogen, alkyl of 1 to 3 carbon atoms or alkoxyalkyl, with 1 to 3 carbon atoms in each of the alkoxy and alkyl portions, $R^3$ is phenyl, -COOAlkyl, -PO$_3$(Alkyl)$_2$, —SO$_2$Aryl, —SO$_2$Alkyl,

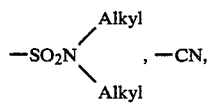

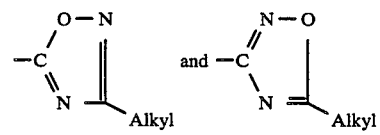

each with 1 to 3 carbon atoms in the alkyl group, comprising reacting an indole of formula II:

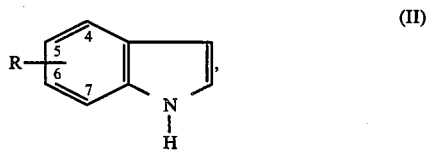

wherein R is as defined for formula I, with an azabutadiene of formula III:

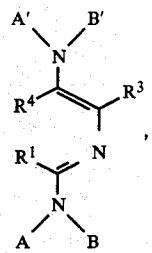

wherein A and B and A' and B', each alone can independently be alkyl of 1 to 3 carbon atoms or together with the connecting N-atom each can independently form a pyrrolidino, piperidino, morpholino or piperazino group and $R^1$, $R^3$ and $R^4$ are as defined for formula I, in the presence of an acid at an effective temperature of 50° to 200° C.

DETAILED DISCUSSION

It has now been found that by reaction of an indole of formula II with an azabutadiene of formula III, the desired β-carbolines of formula I are formed with a good yield. The reaction surprisingly proceeds regiospecifically to form β-carbolines. Secondary reactions, for example, formation of γ-carbolines, are not observed.

The reaction according to this invention takes place in the presence of acids at an effective temperature of 50° to 200° C., preferably 75° to 150° C.

By "effective temperature" is meant a temperature sufficiently high to effect the cyclization. Choice of optimal reaction temperature will be made routinely and conventionally depending on the catalyst or solvent chosen. Also a factor will be the substituents on the indole being used. Electron donor substituted indoles generally react faster and, hence, under more gentle conditions than acceptor substituted indoles. If temperatures less than that effective to cause the cyclizations are used, the resultant reaction and products will be those which are the subject of commonly assigned U.S. application Ser. No. 547,555.

The reaction, for example, is performed such that the indole derivative and azabutadiene are heated in organic acids, for example, formic acid, acetic acid, propionic acid or trifluoroacetic acid, or in inorganic media, for example, phosphoric acid, polyphosphoric acid or phosphorus oxychloride, etc. Inert organic solvents, for example, toluene, ethyl acetate, dioxane, dimethoxyethane, or acetonitrile, among others, can also be used as diluents. But catalytic amounts, e.g., 2–20 molar equivalents based on the compound of formula I, of inorganic acids, e.g., sulfuric acid, hydrochloric acid, perchloric acid, etc., can also be used in inert solvents (as above) for the reaction.

The indole and azabutadiene are used in a molar ratio of 1:1.1–1:1.5. Usually, the concentration of total reactants in the acid and/or inert solvent is 5–50 wt. %. The recation is preferably carried out under an inert atomsphere, e.g., nitrogen.

The acids generally are strong acids characterized by a pH value of <3.

The reaction is stopped after several hours. The course of the reaction can be followed by thin-layer chromatography. The starting material is usually fully reacted after some 3 to 10 hours, whereafter the reaction mixture is worked-up in the usual way.

The process of this invention is generally disclosed in terms of its broad application to the preparation of the compounds of Formula I. Occasionally, for certain substituents R, which will be readily recognized by those skilled in the art, conventional modifications may be necessary, e.g., appropriate protection of interfering groups.

The resulting substituted carboline derivatives can be further substituted by other known chemical processes or the existing substituents can be varied further, also conventionally. Hence, the process according to this invention makes easily available a large number of β-carboline derivatives.

The substituent R in formulae I and II can be in the 5-, 6-, 7- or 8-position or the 4, 5, 6 or 7 position of the aromatic ring. The ring can be mono- or disubstituted with the substituent R. R can be hydrogen, halogen, or any organic radical.

Fluorine, chlorine, bromine and iodine are suitable halogen atoms. Suitable organic radicals preferably include: alkyl, alkoxyalkyl or alkoxy, each of 1 to 4 carbon atoms, methylenedioxy, benzyloxy, aza, cyano or alkoxycarbonyl or dialkylamino, each of 1 to 4 carbon atoms in each alkyl portion. Suitable aryl groups include phenyl, α-or β-naphthyl, etc.

Many other substituents are possible and are disclosed in many references, e.g., DE-OS No. 30 15 816, DE-OS No. 30 23 567, DE-OS No. 30 48 318, U.S. Pat. No. 3,202,667, U.S. Ser. No. 331,740, filed on Dec. 17, 1981, now allowed, and U.S. Pat. No. 4,371,536, all of whose entire disclosures are incorporated by reference herein. The references also disclose in detail the pharmacological utility of all the compounds preparable by the process of this invention.

All of the starting materials are either per se known or are conventionally preparable using fully conventional methods from other known or readily preparable starting materials, e.g., analogous to the methods used for azadienes 1–4 below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

Production of the azadienes of formula III is demonstrated by the following examples:

(1)
3-dimethylamino-2-(dimethylaminomethyleneamino)-ethyl acrylate (azadiene 1)

(a) See preparation according to W. Kantlehner et al., Liebigs Ann. Chem 1980, 344, whose disclosure is incorporated by reference herein.

(b) 3.1 g of freshly distilled glycine ethyl ester is mixed with 17.7 g of dimethylformamidediethylacetal and 0.3 g of potassium tert-butylate and is heated first at 80° C. (bath temperature), then gradually to 160° C. (bath temperature), whereby the resulting alcohol and other readily volatile components are distilled off. After 5 hours, the residue is fractionated in a high vacuum, then distilled once more in a bulb tube. Yield: 3.6 g (54%); boiling point, 150°–160° C. (at 0.05 torr), gas chromatographic purity 97%; $n_d^{25}$ 1.5550.

(2)
3-dimethylamino-2-(dimethylaminomethyleneamino)-crotonic acid-ethyl ester) (azadiene 2)

A mixture of 4.7 g of N(dimethylaminomethylene)-glycine-ethyl ester (W. Kantlehner et al., Liebigs Ann. Chem. 1980, 344), 8 g of dimethylacetamide-dimethylacetal and 0.4 g of potassium tert-butylate, analogously to 1b), is heated for 8 hours with distilling off of the resulting alcohols. The residue is fractionated.

(3)
2-dimethylamino-1-(dimethylaminomethyleneamino)-ethylene-phosphonic acid-diethyl ester (azadiene 3)

A mixture of 3.7 g of aminomethanephosphonic acid-diethyl ester and 15 g of the aminal ester of tert-butoxy-N,N,N',N'-tetramethylmethanediamine is heated for 6 hours to around 160° C. After fractional distillation of the residue in a bulb tube at 160°–165° C. and 0.03 mm, 4.2 g (69%) is obtained.

(4) $N^2$-(2-dimethylamino-1-phenylvinyl)-$N^1$, $N^1$-dimethylformamidine (azadiene 4)

See preparation according to W. Kantlehner et al., Liebigs Ann. Chem., 1980, 344.

The following examples will explain the process according to this invention in more detail:

EXAMPLE 1

β-carboline-3-carboxylic acid-ethyl ester 1.2 g of indole and 3.2 g of 3-dimethylamino-2-(dimethylaminomethylene-amino-ethyl acrylate (azadiene 1) are dissolved under nitrogen in 17 ml of glacial acetic acid and heated at reflux until no initial indole can be seen by thin-layer chromatography (6 hours). After distilling off most of the solvent, it is poured in water and the crystallizate drawn off by suction. After recrystallization from acetonitrile, 1.45 g (60%) of the compound of the title, with a melting point of 234° C., is obtained.

EXAMPLE 2

5-methyl-β-carboline-3-carboxylic acid-ethyl ester

With ice cooling, 22 g of azadiene 1 is added drop by drop to a mixture of 26 ml of trifluoroacetic acid and 90 ml of glacial acetic acid and stirred for 15 minutes under nitrogen. After addition of 11.5 g of 4-methylindole, it is stirred for 17 hours at room temperature, then heated for 2 hours to 150° C. (bath temperature). After distilling off a part of the solvent, the residue is poured into aqueous potassium carbonate solution; the crystalline material is drawn off by suction, washed with water and ether and dried. After recrystallization from ethanol, 17.35 g (79%) of the compound of the title, with a melting point of 264° C., is obtained.

Analogously there are produced:
9-methyl-β-carboline-3-carboxylic acid ethyl ester from N-methylindole and azadiene 1, melting point 140° C. (ethanol), yield: 52% of theory;
6-chloro-β-carboline-3-carboxylic acid ethyl ester from 5-chlorindole and azadiene 1, melting point 292° C. (ethanol), yield: 48%;
5-methyl-β-carboline-3-phosphonic acid-monoethyl ester from 4-methylindole and azadiene 3;
5-cyano-β-carboline-3-carboxylic acid-ethyl ester from 4-cyanoindole and azadiene 1, melting point 304° C., yield: 38%;
8-aza-β-carboline-3-carboxylic acid-ethyl ester from 7-azaindole and azadiene 1, melting point 250° C. (diethylether).

EXAMPLE 3

6-methyl-β-carboline-3-carboxylic acid-ethyl ester

Analogously to example 1, the compound of the title is obtained from 5-methylindole and azadiene 1, with a melting point of 254°–256° C. (from ethanol).

EXAMPLE 4

6-fluoro-β-carboline-3-carboxylic acid-ethyl ester

Analogously to example 1, the compound of the title is obtained from 5-fluoroindole and azadiene 1, with a melting point of 293°–294° C. (from acetonitrile).

EXAMPLE 5

8-methoxy-β-carboline-3-carboxylic acid-ethyl ester

Analogously to example 1, the compound of the title is obtained from 7-methoxyindole and azadiene 1, with a melting point of 273°–274° C. (from toluenetetrahydrofuran).

EXAMPLE 6

6-benzyl-β-carboline-3-carboxylic acid-ethyl ester

Analogously to example 1, the compound of the title is obtained from 5-benzyloxyindole and azadiene 1, with a melting point of 261°–263° C. (from ethanol-tetrahydrofuran).

EXAMPLE 7

5-benzyloxy-β-carboline-3-carboxylic acid-ethyl ester

Analogously to example 1, the compound of the title is obtained from 4-benzyloxyindole and azadiene 1, with a melting point of 281°–283 °C. (from diemthylformamide).

EXAMPLE 8

5-ethoxymethyl-β-carboline-3-carboxylic acid-ethyl ester

Analogously to example 1, the compound of the title is obtained from 4-ethoxymethylindole and azadiene 1.

EXAMPLE 9

5-ethoxymethyl-β-carboline-3-phosphonic acid-diethyl ester

Analogously to example 1, the compound of the title is obtained from 4-ethoxymethylindole and 2-dimethylamino-1-(dimethylaminomethyleneamino)-ethylene-phosphonic acid-diethyl ester (azadiene 3).

EXAMPLE 10

β-carboline-3-phosphonic acid-diethyl ester

Analogously to example 1, the compound of the title is obtained from indole and azadiene 3.

EXAMPLE 11

3-phenyl-β-carboline

Analogously to example 1, the compound of the title is obtained from indole and $N^2$-(2-dimethylamino-1-phenylvinyl)-$N^1$,$N^1$-dimethylformamidine (azadiene 4).

EXAMPLE 12

4-methyl-β-carboline-3-carboxylic acid-ethyl ester

Analogously to example 1, the compound of the title is obtained from indole and 3-dimethylamino-2-(dimethylaminomethyleneamino-crotonic acid-ethyl ester (azadiene 2).

EXAMPLE 13

5-benzyloxy-β-carboline-3-phosphonic acid-diethyl ester

Analogously to example 1, the compound of the title is obtained from 4-benzyloxyindole and azadiene 3.

EXAMPLE 14

β-carboline-3-phosphonic acid-monoethyl ester

Analogously to example 10, the compound of the title is obtained in the presence of catalytic amounts of sulfuric acid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for producing a β-carboline of the formula

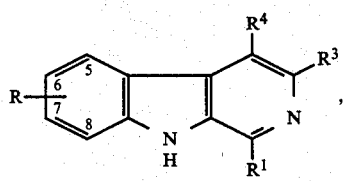
(I)

wherein

R is hydrogen, one or two of halogen atoms or organic substituents in 5-, 6-, 7- or 8-position(s), $R^1$ and $R^4$ are the same or different and each is hydrogen, alkyl of 1 to 3 carbon atoms or $C_{1-3}$-alkoxy-$C_{1-3}$-alkyl, $R^3$ is Phenyl, —COOAlkyl, —PO$_3$(Alkyl)$_2$, —SO$_2$Aryl, —SO$_2$Alkyl,

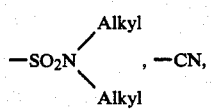, —CN,

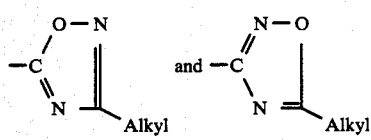

wherein each alkyl group is of 1–3 carbon atoms, comprising reacting an indole of the formula

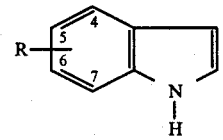

wherein R is as defined above, with an azabutadiene of the formula

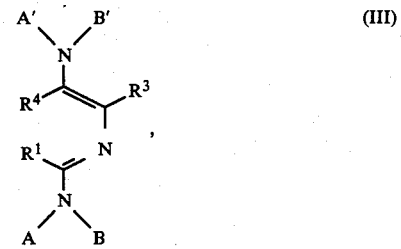
(III)

wherein A, B, A' and B', each independently, is alkyl of 1 to 3 carbon atoms or A and B or A' and B' together with the adjoining N atom form a pyrrolidino, piperidino, morpholino or piperazino group, and $R^1$, $R^3$ and $R^4$ as defined above, in the presence of an acid at an effective temperature of 75° to 200° C.

2. A process of claim 1 wherein the reaction temperature is 75°–150° C.

3. A process of claim 1 comprising heating the indole and the azabutadiene in an organic or inorganic acid.

4. A process of claim 3 wherein the acid is formic acid, acetic acid, propionic acid, trifluoroacetic acid, phosphoric acid, polyphosphoric acid or phosphorus oxychloride.

5. A process of claim 2 wherein the acid is formic acid, acetic acid, propionic acid, trifluoroacetic acid, phosphoric acid, polyphosphoric acid or phosphorus oxychloride.

6. A process of claim 4 wherein the acid component comprises glacial acetic acid.

7. A process of claim 6 wherein the acid component consists essentially of glacial acetic acid and trifluoroacetic acid.

8. A process of claim 5 wherein the acid component comprises glacial acetic acid.

9. A process of claim 1 wherein the reaction is carried out in an inert, reaction compatible solvent.

10. A process of claim 9 wherein the acid component is a catalytically effective amount of a mineral acid.

11. A process of claim 1 wherein the reaction time is 3–10 hours.

12. A process of claim 1 wherein R is H, halo, alkyl, alkoxyalkyl or alkoxy, each of 1 to 4 carbon atoms, methylenedioxy, benzyloxy, aza, cyano or alkoxycarbonyl or dialkylamino, each of 1 to 4 carbon atoms in each alkyl portion.

13. A process of claim 1 wherein $R^3$ is phenyl, —COOalkyl or —PO$_3$(alkyl)$_2$.

14. A process of claim 9 wherein the solvent is toluene, ethyl acetate, dioxane, dimethoxyethane, or acetonitrile.

15. A process for producing a β-carboline of the formula:

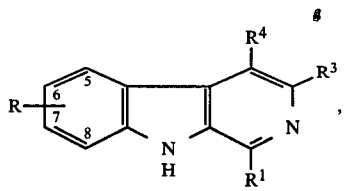
(I)

wherein R is hydrogen, one or two of halogen atoms or organic substituents in 5-, 6-, 7- or 8 -position(s), $R^1$ and $R^4$ are the same or different and each is hydrogen, alkyl of 1 to 3 carbon atoms or $C_{1-3}$-alkoxy-$C_{1-3}$-alkyl, $R^3$ is Phenyl, —COOAlkyl, —$PO_3(Alkyl)_2$, —$SO_2$Aryl, —$SO_2$Alkyl,

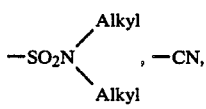

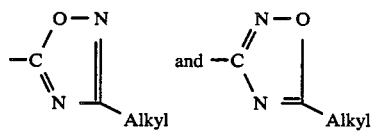

wherein each alkyl group is 1–3 carbon atoms, comprising reacting an indole of the formula

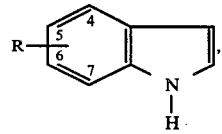
(II)

wherein R is as defined above, with an azabutadiene of the formula (III)

wherein A, B, A' and B', each independently, is alkyl of 1 to 3 carbon atoms or A and B or A' and B' together with the adjoining N atom form a pyrrolidino, piperidino, morpholino or piperazino group, and $R^1$, $R^3$ and $R^4$ are as defined above, in the presence of an acid at a temperature effective to produce predominantly the β-carboline of Formula I.

* * * * *